United States Patent
Hermann

(10) Patent No.: US 8,942,927 B2
(45) Date of Patent: Jan. 27, 2015

(54) SYSTEM AND METHOD FOR QUANTITATIVE ANALYSIS OF THE ELEMENTAL COMPOSITION OF A MATERIAL BY LASER-INDUCED BREAKDOWN SPECTROSCOPY (LIBS)

(75) Inventor: Jörg Hermann, Marseilles (FR)

(73) Assignee: Centre National de la Recherche Scientifique —CNRS—, Paris (FR)

( * ) Notice: Subject to any disclaimer, the term of this patent is extended or adjusted under 35 U.S.C. 154(b) by 936 days.

(21) Appl. No.: 13/128,061

(22) PCT Filed: Oct. 19, 2009

(86) PCT No.: PCT/FR2009/001221
§ 371 (c)(1),
(2), (4) Date: Aug. 22, 2011

(87) PCT Pub. No.: WO2010/052380
PCT Pub. Date: May 14, 2010

(65) Prior Publication Data
US 2012/0029836 A1    Feb. 2, 2012

(30) Foreign Application Priority Data

Nov. 6, 2008  (FR) ..................................... 08 06203

(51) Int. Cl.
*G01N 21/71*   (2006.01)
*G01J 3/443*   (2006.01)

(52) U.S. Cl.
CPC .............. *G01N 21/718* (2013.01); *G01N 21/71* (2013.01); *G01J 3/443* (2013.01)
USPC ........................................... 702/28; 356/318

(58) Field of Classification Search
CPC ..... G01N 21/62; G01N 21/628; G01N 21/71; G01N 21/73; G01N 22/005; G01N 21/718; G01J 3/443

USPC ............................................ 702/28; 356/318
See application file for complete search history.

(56) References Cited

U.S. PATENT DOCUMENTS

| 5,446,538 A | 8/1995 | Noll |
| 5,715,053 A | 2/1998 | Loge |
| 6,657,721 B1 | 12/2003 | Palleschi et al. |

FOREIGN PATENT DOCUMENTS

| DE | 41 18 518 A1 | 12/1992 |
| WO | 97/15811 A1 | 5/1997 |

OTHER PUBLICATIONS

Bulajic et al. "A procedure for correcting self-absorption in calibration free-laser induced breakdown spectroscopy," Spectrochimica Acta Part B 57 (2002) 339-353.*

Hermann et al. "Diagnostics of the early phase of an ultraviolet laser induced plasma by spectral line analysis considering self-absorption," Journal of Applied Physics 83, 691 (1998).*

(Continued)

*Primary Examiner* — Jonathan C Teixeira Moffat
*Assistant Examiner* — Liam R Casey
(74) *Attorney, Agent, or Firm* — Young & Thompson

(57) ABSTRACT

A system and method for measuring elemental concentrations of a material from a sample containing several elements by LIES analysis is provided. The material is heated to generate plasma and its chemical composition is determined from spectral analysis of its radiation. The spectral lines of interest are identified among those emitted by constituents of each element composing sample, and their intensities are measured. The chemical composition of the plasma is calculated. The absorption coefficient according to wavelength is calculated for the spectral zones of the lines of interest. The spectral radiance of the plasma is calculated for the same spectral zones and then a comparison of the intensity and shape of the spectrum thus calculated with those of the spectrum measured is performed. These calculations and this comparison are repeated iteratively in order to adjust the temperature, electron density, relative values of the elemental concentrations and width of the plasma.

7 Claims, 5 Drawing Sheets

(56) References Cited

OTHER PUBLICATIONS

Griem, "Principles of Plasma Spectroscopy," Fast Electrical and Optical Measurements NATO ASI Seriesvol. 108/109, 1986, pp. 885-910.*

Sreckovic et al. "Measured Transition Probabilities in the O II Higher Multiplets," Physica Scripta.vol. 65, 359-362, 2002.*

International Search Report, dated Jan. 8, 2010, from corresponding PCT application.

* cited by examiner

SYSTEM AND METHOD FOR QUANTITATIVE ANALYSIS OF THE ELEMENTAL COMPOSITION OF A MATERIAL BY LASER-INDUCED BREAKDOWN SPECTROSCOPY (LIBS)

The present invention concerns a system and method for quantitative analysis of a material by laser-induced breakdown spectroscopy (LIBS).

TECHNICAL FIELD

The present invention relates to the field of instantaneous measurement by the LIBS technique, without contact or at a distance, of the elemental composition of a material in the solid, liquid or gas form, or in the form of an aerosol. This type of measurement can be used in numerous fields of application, such as waste sorting, measuring pollutants in air or water, analysis of materials in hostile environments such as nuclear ones, detecting explosives or other hazardous materials, interplanetary exploration, etc.

It more particularly relates to a method for quantitative analysis of the elemental composition of a material from a sample having several elements able to generate plasma and emit radiation along a direction of observation.

It also relates to a system for quantitative analysis of the elemental composition of a material from a sample having several elements by laser-induced breakdown spectroscopy measurements.

PRIOR STATE OF THE ART

Such a method and system implement an analysis by the LIBS method. This type of analysis consists of focusing a pulsed laser beam on the surface of a sample of a solid or liquid material (or in a gas) in order to vaporize the material and transform it into a plasma. The plasma emission spectrum is then analyzed in order to determine its chemical composition, which is correlated to that of the material before irradiation. To do so, this analysis relies on measuring the relative intensities of the spectral lines emitted by plasma atoms, ions or molecules.

Determining the elemental composition of the sample from these measurements of the relative intensities of spectral lines requires prior calibration, however. This consists of measuring the intensity ratios between the atomic (or ionic) lines for materials of known composition that is similar to the materials of the unknown sample to be analyzed. In the case, for example, of measuring the carbon concentration in a steel, it is calibrated by measuring the intensity ratio between a carbon line and an iron line for several types of steel containing carbon in different concentrations. The calibration curve obtained then allows determining the carbon concentration in the sample.

A solution of measuring concentration by the LIBS method using a prior calibration is described in patent document WO 97/15811, which concerns a method for determining the concentration of atomic species in a sample. For this, the intensities of at least two spectral lines emitted by the atoms or ions are measured for each element of the sample; this sample is excited by pulsed laser radiation so as to generate plasma and emit radiation. A certain time interval is required in order to consider the plasma to be in local thermodynamic equilibrium and to then be able to instantaneously measure the plasma temperature. The concentration of atomic species to be determined is then deducted from the known emission intensities for the desired atomic species in a predetermined concentration at the measurement temperature. These known emission intensities are determined during prior calibration.

This type of solution, using a prior calibration, mainly poses two problems. On the one hand, the calibration must be done under the same experimental conditions as the measurement of the unknown sample, which involves cumbersome experimental constraints. These constraints are sometimes even impossible to alleviate, like in the case of the dependence of plasma properties on soil humidity, which is generally unknown and therefore impossible to reproduce. Furthermore, calibration requires having as many calibration curves as there are different elements in the unknown sample. Thus, in the case of a sample comprising a high number of elements, the number of calibration curves to create becomes too large.

In order to avoid a prior calibration when measuring elemental concentrations by the LIBS technique from measuring spectral line intensity, a solution is described in patent document U.S. Pat. No. 6,657,721. This solution is based on the calculation of the composition of plasma in local thermodynamic equilibrium (LTE) and the emission coefficient of the spectral lines selected. It is also based on a certain number of assumptions, including: the plasma is optically thin, uniform, completely atomized and in local thermodynamic equilibrium, and stoichiometry is conserved during transformation of the material into plasma. In order to conduct this measurement, the atoms composing the sample are excited and partially ionized by laser radiation in order to generate plasma. The radiation emitted by the plasma is then analyzed without prior calibration, by measuring the intensity of the spectral lines emitted by the atoms (or ions) of each element, obtaining the plasma temperature, determining the concentration of all the species composing an element and multiplying it by a proportion factor, to be calculated from the concentration of each element as the sum of the concentrations of the corresponding species and normalizing each concentration with regard to the sum of all the concentrations, in order to eliminate the proportion factor. This method makes it possible to determine the concentrations of the elements composing the material without needing to do a prior calibration or having reference samples. Furthermore, each measurement is less costly and time consuming, since the method is sufficient by itself.

However, this solution has a certain number of disadvantages. In particular, the assumption according to which the plasma is optimally thin and uniform leads to significant imprecisions in the measurement result. In fact, the assumption of optically thin plasma is never satisfied, since it is in contradiction with that of local thermodynamic equilibrium. This involves a high plasma density, which is especially the case in LIBS plasmas, but it is known that a high density favors absorption by the plasma. Therefore plasma in local thermodynamic equilibrium cannot be considered to be optically thin and self-absorption of spectral lines must be considered. Furthermore, plasma produced by a pulsed laser imposes large temperature and density gradients, which is contrary to a uniformity assumption, where the spatiotemporal variations of plasma temperature and density can be negligible. In the case, for example, of an ablation laser plasma, it has a hot and dense core and a peripheral zone of lower temperature and density. Spectral lines of atoms of high and low ionization potentials are then respectively emitted by the core and the periphery of the plasma. The fact that the spectral emission originates from different temperature zones makes the measurement inaccurate. Consequently, only matter composed of atoms of similar ionization potential can be analyzed without considering the spatial variations of the plasma (U.S. Pat. No. 6,657,721).

Furthermore, the numerical codes proposed for considering the self-absorption of the spectral lines and the spatial non-uniformity of the plasma involve significantly long calculations, which empedes doing measurements in real time.

Therefore no solution of the state of the art allows measuring the concentration of atomic components by LIBS spectroscopy that does not require prior calibration, precisely accounting for the line self-absorption and the spatial non-uniformity of the plasma, and providing a calculation time that can be used for real time measurement.

OBJECTIVE OF THE INVENTION

The goal of the present invention is to alleviate this technical problem, enabling the measurement of concentration without prior calibration and with sufficiently short calculation times, without being limited to assumptions that could cause measurement errors. To do so, it relies on calculating the absorption coefficient of the plasma in order account for the fact that the plasma is not optically thin, as well as rapid calculation of the spectral radiance. The speed of the radiance calculation is obtained by the use of analytical solutions for the radiation transport equation (solutions for one, two or more uniform plasma zones). Rapid iteration of the comparison of the measured and calculated spectra allows obtaining the plasma chemical composition very quickly.

The solution works by considering how to obtain a fast calculation rate from LIBS concentration measurement methods without prior calibration according to the assumptions about the plasma. Therefore it appears that by combining the consideration of the plasma absorption and by using an iterative adjustment of the plasma parameters (width, temperature and electron density of the plasma, relative concentrations of the plasma elements), it was possible to obtain precise measurements of concentration for a fast calculation time.

To this end, the invention relates to a method for quantitative analysis of the elemental composition of a material from a sample comprising several elements that can generate plasma and emit radiation.

Each element has several constituents. The method includes:
- a step of identifying the spectral lines of interest among those emitted by the constituents of each element of the sample,
- a step of measuring the intensities of the spectral lines of interest,
- a step of estimating the plasma temperature,
- a step of estimating the plasma electron density,
- a step of estimating the width of the plasma in the direction of observation,
- a step of calculating the chemical composition of the plasma from temperature and electron density values and values relating to the elemental concentrations of each element of the sample.

This method also includes a step of calculating the absorption coefficient $\alpha(\lambda)$ of the plasma at the spectral lines of interest, a step of calculating the spectral radiance of the plasma and a step of comparing the intensity and shape of the spectrum thus calculated with those of the measured spectrum. The steps of calculating the chemical composition, calculating the absorption coefficient, calculating the spectral radiance and comparing are repeated iteratively. The values for plasma temperature, plasma electron density, plasma width and elemental concentrations are adjusted at each iteration. The iterations continue until a difference is obtained between the intensity and shape of the calculated spectrum and those of the measured spectrum that is less than or equal, in absolute value, to a predetermined threshold value.

This method thus combines considering the absorption of the plasma in order to account for the possibility that the plasma is not optically thin, and an iteration, so as to quickly converge on the most appropriate plasma model according to the desired measurement precision. This makes it possible to obtain both precise concentration measurements and a fast calculation time.

The invention also relies on accounting for temperature and density gradients by dividing the plasma into a set of uniform zones, each zone having a different temperature and electron density. The more zones considered, the more precise the measurement.

Preferably, the method will also include a step of dividing the plasma into an increasing number of zones. This division step depends on obtaining a minimum difference between the intensity and shape of the calculated spectrum and those of the measured spectrum; this minimum being greater, by absolute value, than a predetermined threshold value.

This calculation is first done for a single zone representing uniform plasma. If, after optimizing the parameters, the difference between the intensity and the spectral shape of the lines of interest calculated and those of the measured spectrum is greater, by absolute value, than a predetermined threshold value, the plasma is divided into an increasing number of zones along the direction of observation, each characterized by different temperature and electron density values. The iteration is now done on the adjustment of n+6 (instead of n+3) parameters, the concentrations of n elements and the temperature, electron density and width values for each zone. As a result, the calculated and measured spectra are compared over at least n+6 lines of interest. Other zones can also be added if the result is not yet satisfactory.

This variant of the method advantageously combines dividing the plasma into two or more uniform zones to account for the possibility that the plasma is not uniform, considering the absorption of the plasma in order to account for the possibility that the plasma is not optically thin, as well as an iteration, so as to quickly converge toward the most appropriate model of the plasma according to the desired measurement precision.

This makes it possible to obtain both precise concentration measurements and a fast calculation time.

In the present patent, constituent of an element means any atom, ion and molecule comprised in this element.

Preferably, the spectral radiance of the plasma is calculated by using analytical solutions for the radiation transfer equation. This type of solution allows quickly calculating the plasma radiance by considering its optical thickness, which provides faster and more precise concentration measurements.

According to one preferential embodiment of the temperature estimation step, the temperature is estimated from the ratio of the intensity of the spectral lines emitted by at least one constituent of one element of the sample.

According to one preferential embodiment of the electron density estimation step, the electron density is estimated from measuring the Stark broadening of at least one spectral line.

According to one preferential embodiment of the step of estimating the plasma width in the direction of observation, the width is estimated from measuring the intensity or linewidth of two or more self-absorbed spectral lines of the same multiplet.

Advantageously, the iteration begins with uniform plasma corresponding to a single zone, which allows quickly stopping the calculations if one iteration with a single uniform zone proves to be sufficient.

The invention also relates to a system for quantitative analysis of the elemental composition of a material from a sample having several elements by laser-induced breakdown spectroscopy. Each element has several constituents. This system includes:
- a laser radiation source that can heat the material so as to generate a plasma emitting radiation,
- optical means arranged to direct and focus the radiation from the laser source to the sample,
- an optical system to receive the radiation emitted by the plasma generated by said sample,
- a system for spectroscopic analysis of optical signals,
- a computing device including:
  - means for identifying the spectral lines of interest among those emitted by the constituents of each element of the sample,
  - means for obtaining the intensities of the spectral lines of interest,
  - means for obtaining the plasma temperature,
  - means for obtaining the plasma electron density,
  - means for obtaining the width of the plasma in the direction of observation,
  - means for calculating the chemical composition of the plasma from temperature and electron density values and values relating to the elemental concentrations of each element of the sample.

In this system, the computing device also includes means for calculating the plasma absorption coefficient as a function of the wavelength in the spectral zones selected for the observation of the lines of interest, means for calculating the plasma spectral radiance and means for comparing the intensity and the shape of the spectrum thus calculated with those of the spectrum measured by the spectroscopic analysis system. The means for calculating the chemical composition of the plasma, for calculating the absorption coefficient, for calculating the spectral radiance and for comparing are configured so as to execute the calculations and comparisons successively and iteratively. The values of plasma temperature, plasma electron density, plasma width and the elemental concentrations are adjusted at each iteration. The iterations continue until a difference is obtained between the intensity and shape of the calculated spectrum and those of the measured spectrum that is less than or equal, by absolute value, to a predetermined threshold value.

Preferably, the computing device also has means for dividing the plasma into an increasing number of zones and means for comparing the difference between the intensity and the shape of the calculated spectrum and those of the spectrum measured by the spectroscopic analysis system to the predetermined threshold value. The division means is configured to execute this division as long as the difference obtained between the intensity and shape of the calculated spectrum and those of the measured spectrum is a minimum and said minimum is greater, by absolute value, than the predetermined threshold value.

BRIEF DESCRIPTION OF THE DRAWINGS

The invention will be better understood upon reading the detailed description of one non-limiting example of embodiment, accompanied by figures, respectively showing.

DETAILED DESCRIPTION OF PARTICULAR EMBODIMENTS

Figure 1:
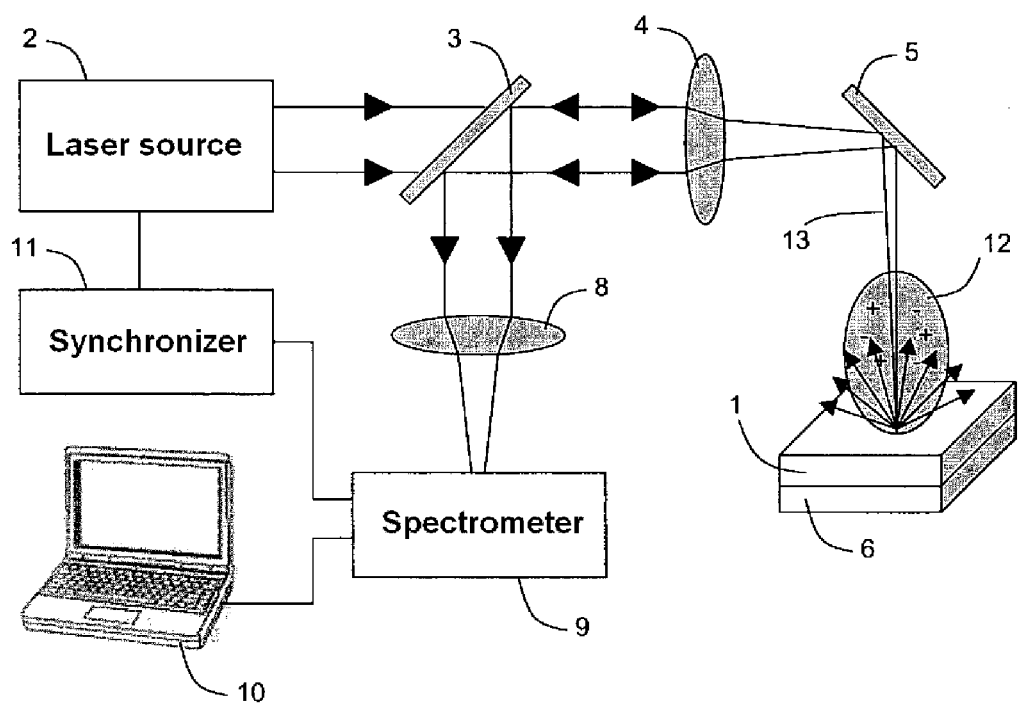
FIG. 1, a diagram of a system for quantitative analysis of the elemental composition of a material according to the invention, FIG. 2, a diagram of a method for quantitative analysis of the elemental composition of a material according to the invention, FIGS. 3 and 4, diagrams of the algorithms for calculating, respectively, the ionization equilibration and the chemical equilibration, permitting calculating the chemical composition of the plasma according to the invention, and FIGS. 5A and 5B, diagrams illustrating the step of dividing the plasma into several uniform zones in the direction of observation.

In reference to FIG. 1, a system for quantitative analysis of the elemental composition of a material according to the invention, also comprising a laser radiation source 2, optical separation means 3, optical means 4 and 5, a stand 6, an optical system 8, a calibrated spectroscopic analysis system 9, a computing device 10 and a synchronizer 11.

Source 2 emits a pulsed laser radiation that crosses beamsplitter 3 before being focused on the surface of sample 1 (or in the gas) via a lens 4 and a mirror 5 properly oriented. The laser radiation heats the material on the surface of sample 1, which generates plasma 12 and induces the emission of radiation 13. A part of radiation 13 emitted by the plasma is collected by means of optical means 4 and 5, and then is reflected by beamsplitter 3 and finally collected by optical system 8 toward spectrometer 9.

Note that the use of a stand 6—or sample holder—is only necessary in the case of a liquid or solid material. In the case of a gas, a sample holder is not needed and the beam can be directly focused in the gas.

Spectrometer 9 performs spectral dispersion and acquisition of plasma radiation 13 collected. To do so, it has a vector or matrix photon detector. It is connected to computing device 10 as well as to synchronizer 11; this synchronizer is also connected to laser source 2 so as to synchronize the laser pulse coming from source 2 and the acquisition of the corresponding optical signals by spectrometer 9. These signals are then transmitted to computer 10, which has a microprocessor for controlling the system, on the one hand, and for executing software dedicated to data analysis by implementing the successive steps of the invention, on the other hand.

The wavelength and intensity of spectrometer 9 are calibrated beforehand. The intensity calibration, consisting of determining the response of the device as a function of wavelength, is done by means of a radiation source whose spectral radiance is known, for example a tungsten lamp or a deuterium lamp.

Computing device 10 comprises a collection of means for performing the various estimates, calculations, comparisons, adjustments and iterations necessary to executing the analysis method according to the invention. These means are in the form of a computer program combined with means for executing this program.

According to one particular embodiment, the system also comprises a database for calculating the partition functions and calculating the absorption coefficient according to wavelength for the spectral zones selected for analysis.

Figure 2:
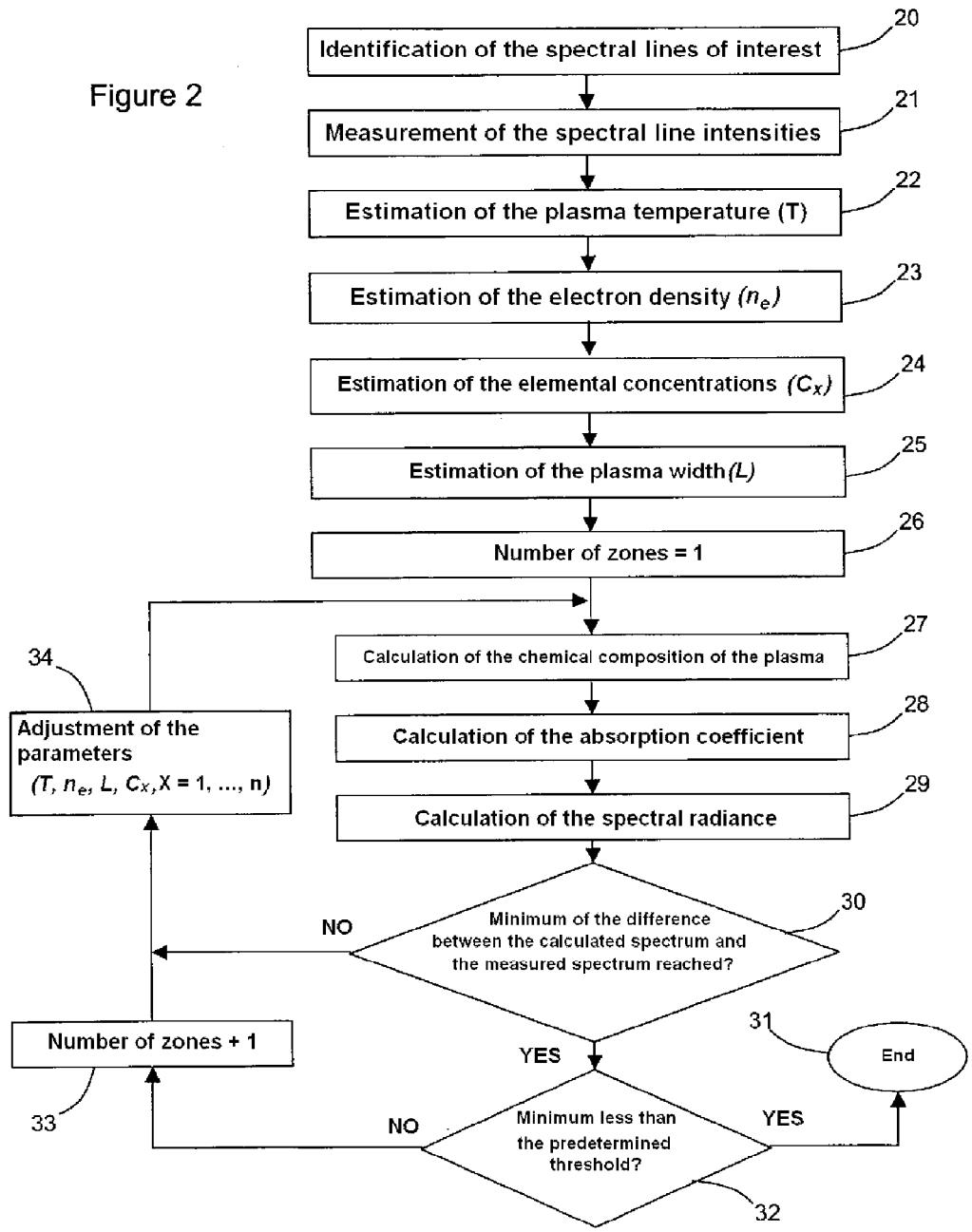

We will now describe one embodiment of the method for measuring elemental concentrations according to the invention in reference to FIG. 2.

This method uses the data from the radiation emitted by plasma 12 and acquired by spectrometer 9. It includes a first step 20 of identifying the spectral lines in the spectrum measured. This identification can be done from a complete database containing all the lines situated in the spectral zones selected for analysis. These zones were defined in a step prior to the spectroscopic measurement, where the lines of interest are chosen. Identification can then be done by comparing the theoretical spectrum to the experimental spectrum.

The spectral lines are thus obtained individually, and the intensities of these lines are measured in step 21. The wavelength at the center of each line and the integral of each line can also be measured.

Then a first estimate 22 of plasma temperature (T) is made from the intensity ratios of appropriate lines, then a first estimate 23 of plasma electron density ($n_e$) is made by measuring the Stark broadening of the line. In the case where the Stark broadening cannot be measured, the electron density can be deduced from the intensity ratio of the lines emitted by a neutral atom and an ion of the same element.

Once these two characteristic values of plasma 12 are obtained, an estimate 24 of n values relative to the concentrations ($C_x$) of the different elements of sample 1 is done. An estimate 25 of the width (L) of plasma 12 in the direction of observation is also done. Note that these estimates can be arbitrary, to the extent that they will be adjusted during future iterations.

The iteration can begin by an initialization step 26 consisting of considering that the number of uniform plasma zones equals 1, which amounts to assuming that the plasma is spatially uniform. The iteration then consists of the succession of steps of calculation 27 of the chemical composition of the plasma, calculation 28 of the absorption coefficient as a function of wavelength for the spectral zones of the lines of interest, calculation 29 of the spectral radiance for the spectral zones of the lines of interest and comparison 30 of the spectrum—calculated from calculation steps 27 to 29 (for n+3 parameters, which are n elemental concentrations, temperature, electron density and thickness of the plasma in the direction of observation) with the spectrum measured. The iteration begins with estimated values for T and $n_e$ and n concentrations and thickness L estimated or chosen arbitrarily.

Step 27 consists of calculating the chemical composition of the plasma from the plasma temperature (T) and electron density ($n_e$) values, as well as values relating to the concentrations (Cx) of the n elements present in the sample to be analyzed. The composition of plasma in local thermodynamic equilibrium is, in fact, determined by its temperature (T) and the atomic densities of the elements. In the typical temperature range for LIBS plasmas, greater than 5000 K, the presence of polyatomic molecules may be negligible. The atomic density of an element X is given by:

$$n_X = n_X^{\#} + \sum_{X=1, X \neq Y}^{N} \sum_{z=0}^{1} n_{XY}^{z} \qquad \text{Equation 1}$$

Where $n_x^{\#}$ is the density of atoms that have not undergone chemical reactions with other elements, $n_{xy}^z$ are diatomic molecules of charge z formed by chemical reactions with other elements Y. We have:

$$n_X^{\#} = \sum_{z=0}^{m} n_X^z + 2 \sum_{z=0}^{1} n_{X_2}^z, \; X = 1, \ldots, N \qquad \text{Equation 2}$$

Where $n_x^z$ and $n_{x2}^z$ are homonuclear atomic and molecular species of charge z. The calculation considers atomic ions with a maximum charge m=3 and singly ionized molecular ions.

Figure 3:
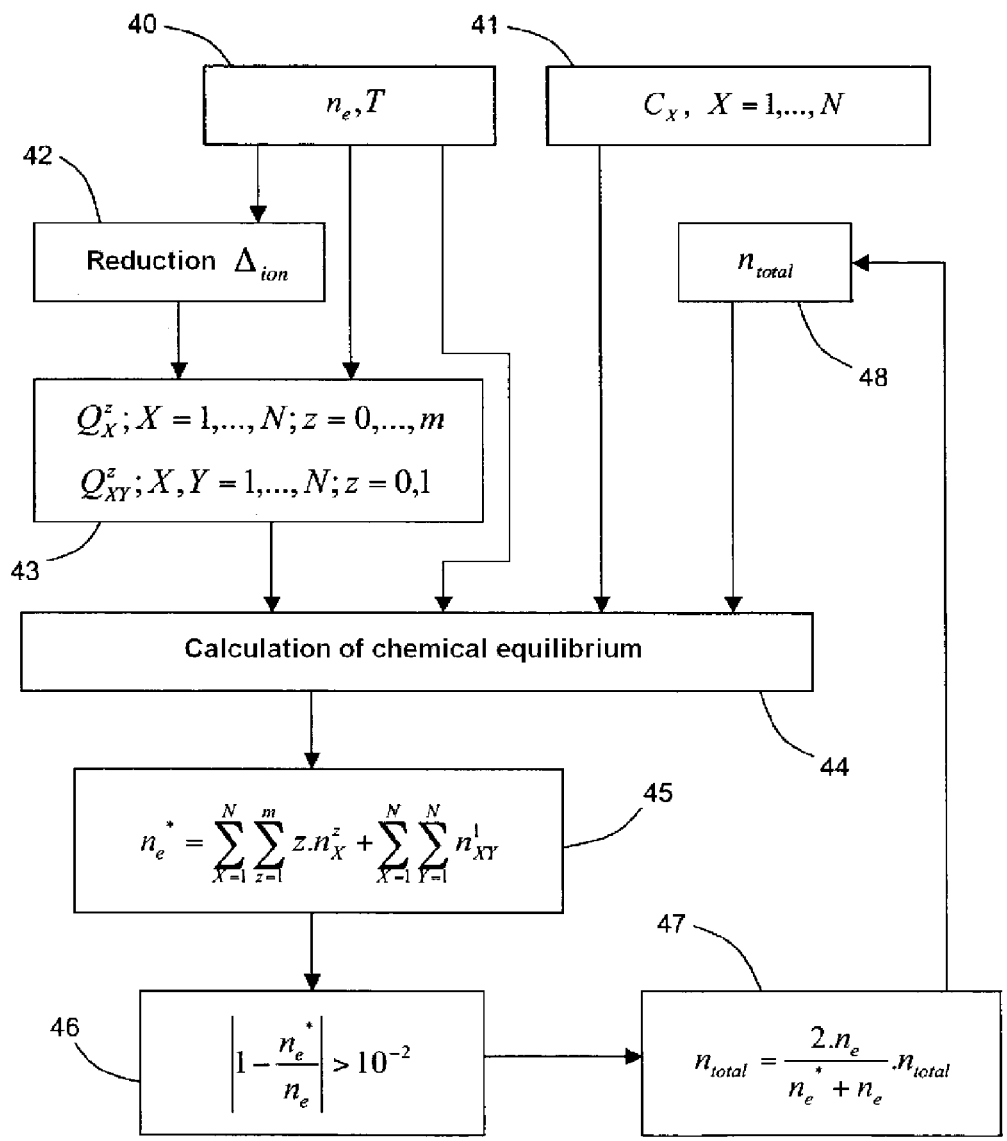
Figure 4:
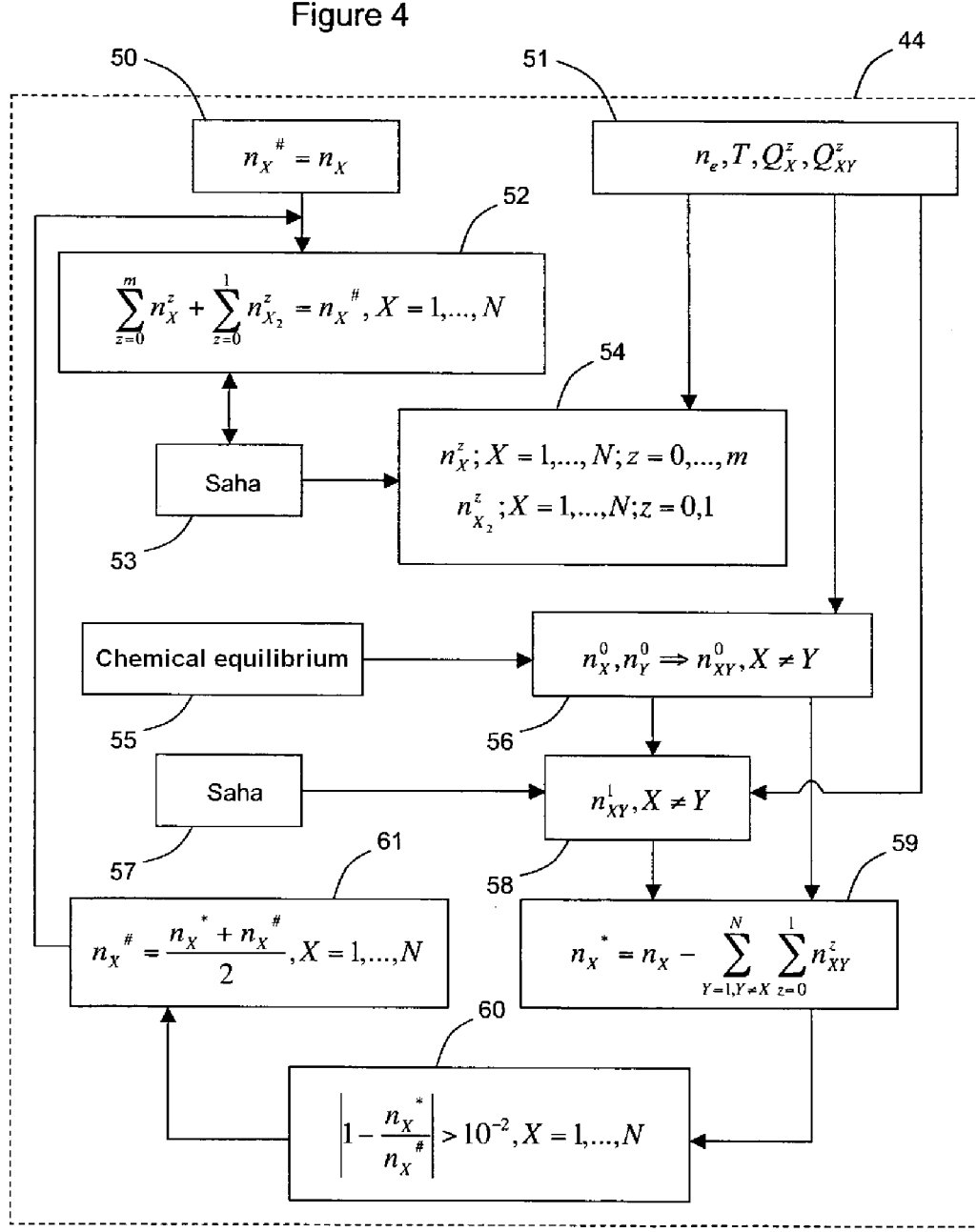

The composition of the plasma in local thermodynamic equilibrium is calculated according to the calculation algorithm presented schematically in FIGS. 3 and 4. A primary iteration loop (FIG. 3) is used to calculate the ionization equilibrium. A secondary iteration loop (FIG. 4) inside the primary iteration loop (see FIG. 3) is used to calculate the chemical equilibrium.

The calculation is done from the values of electron density $n_e$ and temperature T (40) as well as the relative concentrations $C_x$ of the elements (41).

The calculation begins with a total atomic density (48) $n_{total} = n_e$. First, the reduction of the ionization potential $\Delta_{ion}$ is determined (42). Next, the partition functions Q of all the plasma species are calculated (43). The diatomic molecule partition functions are determined by using:

$$Q_{XY}^z = \sum_n (2 - \delta_\Lambda) \cdot (2S+1) \cdot$$

$$e^{-\frac{E(n)}{kT}} \cdot \sum_{v=0}^{v_{max}} e^{-\frac{G(v)}{kT}} \cdot \sum_{J=0}^{J_{max}} g_N \cdot (2J+1) \cdot e^{-\frac{F(J)}{kT}} \qquad \text{Equation 3}$$

Where n is the electron level number, E(n) its energy, $\delta_\Lambda$ the doubling factor $\Lambda$ and S the spin quantum number. $\upsilon$ and J are, respectively, the quantum numbers of the vibrational and rotational levels, gN is the statistical nuclear weight. Vibrational energy G($\upsilon$) and rotational energy F(J) are calculated by using the appropriate formulas. In agreement with the temperature range of interest (T<2. $10^4$ K), the sum of the rotational levels was limited to $J_{max}$=200. The maximum quantum number $\upsilon_{max}$ is determined for each electron level from molecular constants.

After calculating the partition functions, the chemical composition (44) is determined according to the calculation diagram illustrated by FIG. 4.

The calculation uses the parameters $n_e$, T, $Q_X^z$ and $Q_{XY}^z$ (51). The calculation starts by ignoring chemical reactions among the various elements by setting.

$$\sum_{z=0}^{1} n_{XY}^z = 0$$

According to equation 1, we initially have $n_x = n_x^{\#}$ (50). For each element, the densities of the atoms, ions and molecules that do not participate in chemical reactions with other elements (54) are calculated by using the appropriate Saha equations (53) respecting the law of conservation of mass (52) Then the densities of the diatomic molecules resulting from chemical reactions among various elements (56) are determined by using the law of mass action for chemical equilibration (55):

$$\frac{n_X^0 \cdot n_Y^0}{n_{XY}^0} = \frac{(2\pi\mu kT)^{3/2}}{h^3} \cdot \frac{Q_X^0 \cdot Q_Y^0}{Q_{XY}^0} \cdot e^{-\frac{D_0}{k\cdot T}}$$ Equation 4

Where $n^0_x$ and $n^0_y$ are, respectively, the densities of the neutral atoms of elements X and Y and $n^0_{xy}$ is the density of the diatomic molecules resulting from the chemical reaction between the two elements. $Q^0_x$, $Q^0_y$, and $Q^{0x}_y$ are the corresponding partition functions. $D_o$ is the dissociation energy of molecule XY in the fundamental state, h Planck's constant and $$\mu = \frac{mxmy}{mx+my}$$

the reduced mass calculated from the atomic masses mx and my of the two elements. The densities of ionized molecules $n^1_{xy}$ (58) are calculated by using the corresponding Saha equations (57). After determining the densities of the chemical reaction products, values $n_x^*$ are determined by taking away $n^z_{x=y}$ from $n_x$ according to equation 1 (59). If the difference between $n_x^\#$ and $n_x^*$ is too great for at least one element (60), the calculation is repeated with the mean value of $n_x^\#$ and $n_x^*$ (61). After calculating the chemical composition, the electron density between $n_e^*$ is determined from neutrality equation (45) as indicated in FIG. 3. If the deviation between $n_e$ and $n_e^*$ is too great (46), the calculation is repeated with an appropriate $n_{total}$ value (47).

Step 28 consists of calculating the plasma absorption coefficient for all the lines situated in the spectral zones selected (around the lines of interest) according to wavelength, by using:

$$\alpha(\lambda) = \pi \cdot r_0 \cdot \lambda^2 \cdot f_{lu} \cdot n_l \cdot P(\lambda) \cdot [1 - e^{-\frac{hc}{\lambda\cdot k\cdot T}}]$$ Equation 5

Where ro is the classical electron radius, c the speed of light, $f_{lu}$, and $n_1$ are respectively the absorption oscillator strength and the population density at the lower level of the transition. The normalized profile $P(\lambda)$ is calculated by considering the Doppler and Stark effects, which are the preponderant mechanism for broadening spectral lines in strongly ionized LIBS plasmas. According to the relative Doppler and Stark values, the spectral shape is approximated by a Gaussian or Lorentzian function or by a Voigt profile. The Doppler width is calculated in accordance with the plasma temperature and the atomic mass of the emitting species. The linewidth and Stark shift are determined for each line.

Step 29 consists of calculating the spectral radiance of the plasma by using analytical solutions for the radiation transfer equation. For the case of a uniform spatial distribution, the plasma radiance is given by:

$$I(\lambda)=U(\lambda)\cdot(1-e^{-\alpha(\lambda)\cdot L})$$ Equation 6:

Where L is the width of the plasma in the direction of observation, $U(\lambda)$ is the blackbody radiance, and spectral luminance $I(\lambda)$ is calculated from all the spectral ranges selected containing the lines of interest. In order to compare the calculated spectrum to the spectrum measured by spectrometer 9, the intensity of the calculated spectrum is adjusted to that of the measured spectrum by multiplying $I(\lambda)$ by a corrective factor that is determined from a reference line.

Comparison (30) is done in all the spectral ranges selected by adjusting the n+3 parameters (T, $n_e$, L and the n relative concentrations $C_x$) in order to determine if the plasma composition allows generating the spectrum measured. During this comparison (30), both the intensity and the shape of the calculated and measured spectral lines are compared. If, this difference is less than a predetermined threshold, the method is terminated (31) and the elemental composition of the plasma is deduced with sufficient precision, this composition being equal to that of the sample. Predetermined threshold means here a collection of criteria formed by several thresholds so as to consider both the intensity and the shape of the calculated and measured spectrum.

If, after optimization of the n+3 parameters, this difference is greater than the predetermined threshold, it is necessary to increase the number of zones of the plasma. At each new iteration, adjustment 34 of the n+3 parameters is done: the plasma temperature, the plasma electron density, the elemental concentrations of each element of the sample as well as the plasma width in the direction of observation. Then calculation steps 27 to 29 are started again, followed by the step of comparison with the adjusted parameters. These iterative steps are repeated for all the spectral zones containing the lines of interest until the threshold discussed above is reached.

We will now describe adjustment step 34. Since self-absorption can lead to a reduction of line intensity (whose magnitude differs from one line to another), the ratio of the intensity of the lines chosen for determining the temperature is examined. If the intensity ratio of the theoretical spectrum is different from that of the measured spectrum, the temperature is adjusted in order to minimize the intensity ratio deviation. In a similar way, since self-absorption can lead to line broadening, the linewidth of the line chosen for the measurement of $n_e$ is examined. If there is a deviation between the calculated linewidth and the measured linewidth, $n_e$ is adjusted in order to minimize the deviation between the two widths. Next, the intensities of the lines chosen for measuring relative concentrations $C_x$ of the n elements are examined one after the other. If there is a deviation between the calculated intensity and the measured intensity, the relative concentration of the corresponding element is adjusted with regard to the majority element that serves as a reference. Next, plasma width L is adjusted from the intensity ratio of the lines of the same multiplet having different self-absorption probabilities.

After having adjusted L, a comparison of the line intensity ratio used to determine T is done again, at a comparison of linewidth chosen for determining $n_e$ and at the comparison of line intensities chosen for determining n elemental concentrations. Since adjusting the concentration of the constituent chosen for determining L changes the line self-absorption effect, the width of the plasma is adjusted again to obtain the intensity ratio of lines chosen for this purpose. Then the parameters are adjusted until the deviation between the calculated and measured spectra are minimized.

In the preferred embodiment of the invention, the parameters adjusted during the iteration are optimized in order to obtain (step 30) a minimum of difference between the calculated and measured intensity and shape of the spectral lines identified. When this minimum is reached (step 32), it is compared with the predetermined threshold value. If the minimum is less than or equal to the threshold value, the method is terminated (step 31). Otherwise, the optimization of parameters is no longer useful. Then a step (33) of increasing the number of plasma zones 12 is done. In this way, the calculation precision is improved by adding one or two (according to the observation geometry) plasma zones in order to account for the non-uniformity of the plasma. Then the iterations can be repeated with this new plasma, by again seeking a minimum of the difference between the intensity and shape of the calculated and measured spectral lines identified, and so on until a minimum of the difference is obtained that is less than or equal to the predetermined threshold value.

Figure 5A:
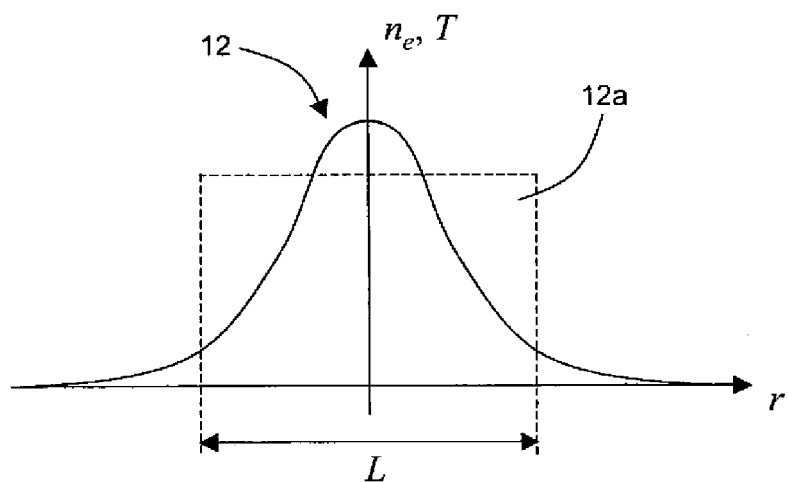
Figure 5B:
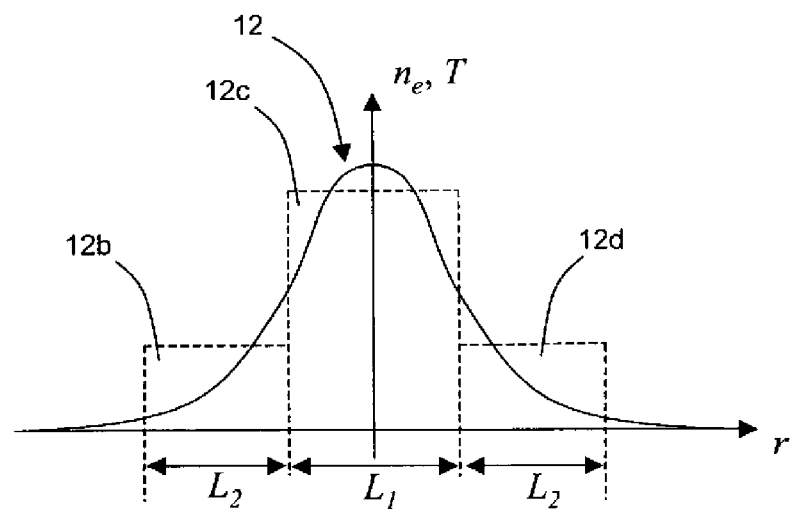

Such a division is illustrated by FIGS. 5A and 5B. FIG. 5A shows a plasma 12 made up of a single uniform zone 12a. FIG. 5B shows plasma 12 divided into three zones 12b, 12c and 12d in which the temperature and electron density are supposed to be spatially uniform.

In the case, for example, where the plasma is divided into two uniform zones, one may be considered to represent the hot and dense core (1) and the other the peripheral zone with lower temperature and density (2). The integration of the radiation transport equation then gives:

$$I = U_1 \cdot (1-e^{-\alpha_1 \cdot L_1}) l^{-\alpha_2 \cdot L_2} + U_2 \cdot (1-e^{-\alpha_2 \cdot L_2})$$
Equation 7:

This expression can be applied to LIBS measurements independently of the observation geometry. Compared to the calculation of radiance of uniform plasma (equation 6), the precision of LIBS measurements is significantly improved for a reasonable increase in calculation time.

The calculated and measured spectra are then compared by adjusting n+6 (instead of n+3) parameters. In this case, at least n+6 spectral lines are used for the comparison between the calculated and measured spectra.

Preferably, the spectral lines emitted by constituents with high ionization potential are used to determine the parameters T, $n_e$ and L of the hot zone, while the spectral lines emitted by constituents of low ionization potential are chosen to determine the same parameters for the cold zone.

In the majority of applications of the present method, the n relative concentrations Cx are assumed to be equal in all the zones, conforming to the assumption of negligible segregation in the plasma. However, it is possible to consider a possible segregation, such as, for example, segregation by diffusion of light elements in the case of LIBS analysis under reduced atmosphere (such as LIBS analysis on Mars) by using several zones and adjusting the relative concentrations to take into account the different spatial distribution of elements due to segregation. In this case, a supplemental equation describing the segregation phenomenon will be added in order to make the calculation converge rapidly.

Note that the following 34 adjustments are done in each of the zones defined within the plasma, in order to refine the measurement result.

According to this concentration measurement method, for a solid (or liquid or gaseous) material composed of n different elements and plasma divided into m uniform zones, the calculation therefore involves n+3m parameters to be adjusted. These parameters correspond to the relative concentrations of n elements, as well as temperature T, electron density $n_e$ and the dimension along the axis of observation L of each of the m zones of the plasma.

The present invention also considers the possibility of accounting for the temporal variation of parameters T, $n_e$, and L. This is necessary when the measurement cannot be done with a sufficient temporal resolution and the spectrum measured corresponds to the radiation generated by plasma whose temperature, electron density or width varies throughout the duration of acquisition. In this case, similar to the way the parameters' spatial variation is considered, it is divided into one or more temporal windows. The total radiance is obtained by simple addition of the radiances calculated for each temporal window from equations 6 or 7.

The previously described modes of embodiment of the present invention are given by way of example and are not at all limiting. It is understood that those skilled in the art can produce different variants of the invention without exceeding the scope of the patent.

The invention claimed is:

1. A method for quantitative analysis of the elemental composition of a material from a sample having a plurality of elements able to generate plasma and emit radiation, each element containing several constituents, the method comprising:
   heating the material from the sample to generate the plasma configured to emit the radiation;
   measuring the emitted radiation to obtain a spectrum;
   identifying, from the obtained spectrum, spectral lines of interest among spectral lines emitted by the constituents of each element of the heated sample;
   measuring intensities of the spectral lines of interest;
   estimating a temperature of the plasma;
   estimating an electron density of the plasma;
   estimating a dimension of the plasma along the direction of observation;
   calculating a chemical composition of the plasma from the temperature and the electron density values and values relating to the elemental concentrations of each element of the sample; calculating an absorption coefficient of the plasma at the spectral lines of interest;
   calculating a spectral radiance of the plasma;
   calculating a spectrum from the calculated chemical composition, the calculated absorption coefficient, and the calculated spectral radiance of the plasma;
   comparing the intensity and the shape of the calculated spectrum thus calculated with the intensity and the shape of the measured spectrum;
   iteratively repeating the calculation of the chemical composition, the calculation of the absorption coefficient, the calculation of spectral radiance, the calculation of the spectrum, and the comparison wherein the values of the temperature of the plasma, the electron density of the plasma, the dimension of the plasma, and the elemental concentrations being adjusted at each iteration until a difference is obtained between the intensity and the shape of the calculated spectrum and the intensity and the shape of the measured spectrum that is less than or equal, by absolute value, to a predetermined threshold value; and
   dividing the plasma into an increasing number of zones, when a minimum of the difference between the intensity and the shape of the calculated spectrum and the intensity and the shape of the measured spectrum is obtained, the minimum being greater, by absolute value, than the predetermined threshold value.

2. The method according to claim 1, wherein the spectral radiance of the plasma is calculated by using analytical solutions for the radiation transfer equation.

3. The method according to claim 1, wherein the temperature is estimated from the ratio of the intensity of the spectral lines emitted by at least one constituent of one element of the sample.

4. The method according to claim 1, wherein the electron density is estimated from a measurement of the Stark broadening of at least one spectral line.

5. The method according to claim 1, wherein the dimension of the plasma along the direction of observation is estimated from measuring the intensity or the spectral width of two or more self-absorbed lines of the same multiplet.

6. The method according to claim 1, wherein the iteration begins with uniform plasma corresponding to a single zone.

7. A system for quantitative analysis of the elemental composition of a material from a sample containing a plurality of elements by laser-induced breakdown spectroscopy, each element having several constituents, the system comprising:
- a laser radiation source that can heat the material so as to generate plasma emitting radiation;
- optical means configured to direct and focus the radiation from the laser source to the sample;
- an optical system configured to receive the radiation emitted by the plasma generated by the sample;
- a system for spectroscopic analysis of optical signals by measuring the emitted radiation to obtain a spectrum;
- a computing device comprising:
  - means for identifying, from the obtained spectrum, the spectral lines of interest among spectral lines emitted by the constituents of each element of the sample,
  - means for measuring intensities of the spectral lines of interest,
  - means for estimating a temperature of the plasma,
  - means for estimating an electron density of the plasma,
  - means for estimating a dimension of the plasma along the direction of observation,
  - means for calculating the chemical composition of the plasma from the temperature and the electron density values and values relating to the elemental concentrations of each element of the sample,
  - means for calculating the absorption coefficient of the plasma according to the wavelength in spectral zones selected for observing the spectral lines of interest,
  - means for calculating a spectral radiance of the plasma,
  - means for calculating a spectrum from the calculated chemical composition, the calculated absorption coefficient, and the calculated spectral radiance of the plasma,
  - means for comparing the intensity and the shape of the calculated spectrum with the intensity and the shape of the measured spectrum,
  - the means for calculating the chemical composition of the plasma, the means for calculating the absorption coefficient, the means for calculating the spectral radiance, and the means for comparing are configured so as to execute calculations and comparisons successively and iteratively, wherein the values of the temperature of the plasma, the electron density of the plasma, the dimension of the plasma, and elemental concentrations being adjusted at each iteration until a difference is obtained between the intensity and the shape of the calculated spectrum and the intensity and shape of the measured spectrum that is less than or equal to, by absolute value, a predetermined threshold value, and
  - means for dividing the plasma into an increasing number of zones, the division means being configured to execute the division when the difference obtained between the intensity and the shape of the calculated spectrum and the intensity and the shape of the measured spectrum is a minimum, the minimum being greater, by absolute value, than the predetermined threshold value.

* * * * *